United States Patent
Uemori et al.

(10) Patent No.: US 6,673,578 B1
(45) Date of Patent: Jan. 6, 2004

(54) METHOD FOR SYNTHESIZING DNA

(75) Inventors: Takashi Uemori, Otsu (JP); Yoshimi Sato, Shiga (JP); Mariko Okawa, Otsu (JP); Tomoko Fujita, Takatsuki (JP); Kazue Miyake, Uji (JP); Osamu Takeda, Hikone (JP); Hiroaki Sagawa, Kusatsu (JP); Michio Hagiya, Otsu (JP); Hiroyuki Mukai, Moriyama (JP); Kiyozo Asada, Shiga (JP); Ikunoshin Kato, Uji (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/786,684

(22) PCT Filed: Sep. 6, 1999

(86) PCT No.: PCT/JP99/04815

§ 371 (c)(1),
(2), (4) Date: Aug. 29, 2001

(87) PCT Pub. No.: WO00/14218

PCT Pub. Date: Mar. 16, 2000

(30) Foreign Application Priority Data

| Sep. 8, 1998 | (JP) | 10-254277 |
| Oct. 9, 1998 | (JP) | 10-288534 |
| Oct. 12, 1998 | (JP) | 10-289879 |
| Oct. 12, 1998 | (JP) | 10-289880 |
| Dec. 18, 1998 | (JP) | 10-361456 |

(51) Int. Cl.$^7$ .............................. C12P 19/34; C12Q 1/68
(52) U.S. Cl. ........................................... 435/91.2; 435/6
(58) Field of Search ........................... 435/6, 91.2

(56) References Cited

U.S. PATENT DOCUMENTS

| 5,231,015 A | 7/1993 | Cummins et al. |
| 5,403,707 A | 4/1995 | Atwood et al. |
| 5,436,149 A | * 7/1995 | Barnes ...................... 435/194 |

FOREIGN PATENT DOCUMENTS

| EP | 0 511 712 A1 | 11/1992 |
| EP | 0 648 845 A2 | 4/1995 |
| EP | 0 745 687 A1 | 12/1996 |
| EP | A2745675 | 12/1996 |
| JP | A3133379 | 6/1991 |
| JP | A6319597 | 11/1994 |
| JP | A8322597 | 12/1996 |
| JP | A10004963 | 1/1998 |

OTHER PUBLICATIONS

Zhu et al., Transplantation, vol. 58, No. 10, pp. 1104–1109 (1994).

Cheng et al., Proc. Nat'l Acad. Sci., vol. 91, pp. 5695–5699 (1994).

T. Demeke et al., Biotechniques, vol. 12, No. 3, 1992, pp. 332–334, XP001146879.

E. Beutler et al., Biotechniques, vol. 9, No. 2, 1990, p. 166, XP000617725.

* cited by examiner

*Primary Examiner*—Jeffrey Fredman
(74) *Attorney, Agent, or Firm*—Birch, Stewart, Kolasch & Birch, LLP

(57) ABSTRACT

A DNA synthesis method with a shortened time period required for DNA synthesis by polymerase chain reaction (PCR), characterized in that a DNA polymerase is used in an amount effective for providing more than 10 ng of amplified DNA fragments of about 2 kb per 50 μl of a reaction mixture, when PCR is carried out under the following conditions (A) and (B): (A) reaction mixture: 50 μl volume of a reaction mixture comprising DNA polymerase, 1 ng of genomic DNA from *Escherichia coli*, and 10 pmol each of primers Eco-1 and Eco-2 (nucleotide sequences of the primers Eco-1 and Eco-2 being shown in SEQ ID NOs: 10 and 11 of Sequence Listing, respectively); and having a composition suitable for the DNA polymerase; and (B) reaction conditions: 35 cycles of PCR, wherein one cycle consists of 99° C., 1 second–66° C., 7 seconds; a kit for DNA synthesis usable for the DNA synthesis method; and an article of manufacture of a PCR agent. According to the present invention, the procedures in the genetic engineering studies and industries involved with PCR can be speeded up.

9 Claims, No Drawings

METHOD FOR SYNTHESIZING DNA

This application is the national phase under 35 U.S.C. §371 of PCT International Application No. PCT/JP99/04815 which has an International filing date of Sep. 6, 1999, which designated the United States of America.

TECHNICAL FIELD

The present invention relates to a method for DNA synthesis, a kit usable for the method and an article of manufacture, which are useful in the field of genetic engineering, and are capable of shortening a time period needed for polymerase chain reaction (PCR) method.

BACKGROUND ART

The synthesis of DNA is used for various purposes in the research of the field of genetic engineering. Among them, much of the DNA syntheses are carried out by the enzymatic method utilizing DNA polymerase, except for chemical synthesis of a short strand DNA such as an oligonucleotide. Accordingly, the DNA polymerase is highly valuable as reagents for DNA sequencing, DNA labelling, and site-directed mutagenesis.

In addition, recently, with the development of PCR method, thermostable DNA polymerases have attracted attention, and various kinds of DNA polymerases suitable for PCR method have been developed and commercialized.

Furthermore, there is known a method capable of carrying out an efficient DNA synthesis by using a combination of plural DNA polymerases, wherein the efficient DNA synthesis could not be achieved by a single DNA polymerase [*Proc. Natl. Acad. Sci. USA*, 91, 5695–5699 (1994)].

The method is a method using a mixture of DNA polymerases for PCR, the mixture comprising DNA polymerase having 3'→5' exonuclease activity (for example, α-type DNA polymerase derived from *Pyrrococcus furiosus*) and DNA polymerase not having the exonuclease activity (for example, DNA polymerase derived from *Thermus aquaticus* (Taq DNA polymerase), and is known as LA-PCR method.

According to this method, the yield of amplified DNA is increased, as compared with that by conventional PCR using only one kind of DNA polymerase. The method can also amplify long DNA fragment, which could not be amplified by conventional PCR.

Optimum PCR conditions which have been conventionally and generally performed are shown in Table A. The amplification of each DNA is terminated at a reaction time of about 90 minutes in the 1 kbp amplification, at a reaction time of about 268 minutes in the 10 kbp amplification, and at a reaction time of about 478 minutes in the 20 kbp amplification.

TABLE A

Enzyme: TaKaRa Ex Taq[*1] [1.25 U/50 μl (PCR Reagent Mixture)]
Template DNA: *E. coli* Genomic DNA[*2] [100 ng/50 μl (PCR Reagent Mixture)]

| | | | |
|---|---|---|---|
| Amplification of 1 kbp Fragment | 94° C. 55° C. 72° C. | 30 sec. 30 sec. 1 min. | 30 cycles (about 90 minutes) |
| Amplification of 10 kbp Fragment | 98° C. 68° C. | 10 sec. 8 min. | 30 cycles (about 268 minutes) |

TABLE A-continued

Enzyme: TaKaRa Ex Taq[*1] [1.25 U/50 μl (PCR Reagent Mixture)]
Template DNA: *E. coli* Genomic DNA[*2] [100 ng/50 μl (PCR Reagent Mixture)]

| | | | |
|---|---|---|---|
| Amplification of 20 kbp Fragment | 98° C. 68° C. | 10 sec. 15 min. | 30 cycles (about 478 minutes) |

[*1]Product manufactured by Takara Shuzo Co., Ltd.
[*2]genome DNA set for LA PCR ™, manufactured by Takara Shuzo Co., Ltd.

Since the PCR method has an ability to amplify a trace amount of DNA into several millions times the amount in a short time period, the PCR method is applied to all sorts of studies, tests and clinical fields including medical science and agriculture. Particularly, the PCR method is powerful in genetic diagnosis of infectious diseases such as cancers and AIDS, and the like. In addition, its application has been extended even to city life, including confirmation of a guilty party, or a parent-and-child relationship by genetic diagnosis; a gene detection of harmful bacteria in foods, and the like.

However, it has become an important problem to further shorten a reaction time period of PCR and to speed up PCR in food examination for which a quick result is demanded, and in a clinical test in which PCR is required to be carried out on a large scale.

Further, PCR procedures are indispensable for DNA chip preparation, genome analysis and the like, so that it is important to improve its efficiency in view of efficiently carrying out a whole research.

DISCLOSURE OF INVENTION

An object of the present invention is to provide a DNA synthesis method, a kit for use in the synthesis method and an article of manufacture, for carrying out rapid PCR with a more shortened time period as compared with conventional PCR.

A first invention of the present invention relates to a DNA synthesis method with a shortened time period required for DNA synthesis by polymerase chain reaction (PCR), characterized in that DNA polymerase is used in an amount effective for providing more than 10 ng of amplified DNA fragments of about 2 kb per 50 μl of a reaction mixture, when PCR is carried out under the following conditions (A) and (B):

(A) reaction mixture: 50 μl volume of a reaction mixture comprising DNA polymerase, 1 ng of genomic DNA from *Escherichia coli*, and 10 pmol each of primers Eco-1 and Eco-2 (nucleotide sequences of the primers Eco-1 and Eco-2 being shown in SEQ ID NOs: 10 and 11 of Sequence Listing, respectively); and having a composition suitable for the DNA polymerases; and (B) reaction conditions: 35 cycles of PCR, wherein one cycle consists of 99° C., 1 second –66° C., 7 seconds.

A second invention of the present invention relates a kit for DNA synthesis usable for the DNA synthesis method of the first invention of the present invention, characterized in that a PCR reagent mixture which is prepared in accordance with instructions of the kit, comprises a DNA polymerase in an amount effective for providing more than 10 ng of amplified DNA fragments of about 2 kb per 50 μl of a reaction mixture, when PCR is carried out under the following conditions (A) and (B):

(A) reaction mixture: 50 μl volume of a reaction mixture comprising DNA polymerase, 1 ng of genomic DNA from *Escherichia coli,* and 10 pmol each of primers Eco-1 and Eco-2 (nucleotide sequences of the primers Eco-1 and Eco-2 being shown in SEQ ID NOs: 10 and 11 of Sequence Listing, respectively); and having a composition suitable for the DNA polymerase; and (B) reaction conditions: 35 cycles of PCR, wherein one cycle consists of 99° C., 1 second–66° C., 7 seconds.

A third invention of the present invention relates to an article of manufacture of a PCR agent, comprising packaging material and a PCR reagent contained within the packaging material, wherein the PCR agent comprises DNA polymerases, and wherein a label or instruction indicates that the PCR reagent can be used for PCR in a short time period, the label being attached to the packaging material, and the instruction being enclosed with the packaging material.

BEST MODE FOR CARRYING OUT THE INVENTION (1) DNA Synthesis Method of the Present Invention The DNA synthesis method of the present invention is a DNA synthesis method with a shortened time period for synthesizing DNA by PCR method, namely rapid PCR, characterized in that DNA polymerase is used in an amount effective for providing more than 10 ng of amplified DNA fragments of about 2 kb per 50 µl of reaction mixture, when PCR is carried out under the following conditions (A) and (B):

(A) reaction mixture: 50 µl volume of a reaction mixture comprising DNA polymerase, 1 ng of genomic DNA from *Escherichia coli,* and 10 pmol each of primers Eco-1 and Eco-2 (nucleotide sequences of the primers. Eco-1 and Eco-2 being shown in SEQ ID NOs: 10 and 11 of Sequence Listing, respectively); and having a composition suitable for the DNA polymerase; and (B) reaction conditions: 35 cycles of PCR, wherein one cycle consists of 99° C., 1 second–66° C., 7 seconds.

According to the DNA synthesis method of the present invention, since "effective amount of DNA polymerase" is used, there can be shortened a time period required in synthesis reaction of complementary strand corresponding to a given size of DNA fragment (extension step), i.e. there can be shortened a time period required in 1 cycle of reaction. As a result, there are exhibited excellent effects that in PCR, a desired DNA fragment can be amplified in a short time period which has not been achieved conventionally, in other words, rapid PCR can be carried out with a shortened total time period required in PCR.

In the present invention, the term "effective amount of DNA polymerase" means an amount of a DNA polymerase which is an amount corresponding to a sufficient activity such that an amount of a DNA fragment of about 2 kb is more than 10 ng per 50 µl volume of a reaction mixture, when a 35 cycle PCR is carried out by using 50 µl of a reaction mixture containing 1 ng of *E. coli* genomic DNA, and 10 pmol each of primers Eco-1 and Eco-2 (nucleotide sequences of primers Eco-1 and Eco-2 being shown in SEQ ID NOs: 10 and 11 of Sequence Listing, respectively), wherein one cycle consists of 99° C., 1 second–66° C., 7 seconds. Therefore, as long as an amount of DNA polymerase is an amount capable of carrying out PCR under these conditions, an amount of its protein is not limited. The use of this effective amount of DNA polymerase can speed up the PCR.

The term "*E. coli* genomic DNA" described in the present specification includes, for example, genomic DNA prepared from *E. coli* strain JM109 (*Escherichia coli* JM109) according to the method described in "*IDENSHI•TANPAKUSHITSU JIKKENSOUSA BLOTTING (Gene•Protein Experimental Manipulation and Blotting)*" coauthored by Yoshiyuki Kuchino, Hisamaru Hirai, and Ikunosuke Sakuragi, 1987, published by Soft Science Company. In addition, the details of the preparation method are described in *Bio View,* 13, 6–5 (1994, published by Takara Shuzo Co., Ltd.). Furthermore, the genomic DNA is available as genome DNA set for LA PCR™ from Takara Shuzo Co., Ltd.

Incidentally, as a composition of a reaction mixture, there may be used a reaction mixture having a composition suitable for DNA polymerase used. Here, the term "composition suitable for DNA polymerase" means a composition capable of providing optimum conditions such as optimum kinds of buffers, optimum pH, optimum salt concentration (magnesium salt, and the like), optimum dNTPs concentration, optimum amount of primers and other additives.

Here, an enzyme activity unit of DNA polymerase is expressed as an index an ability of catalyzing the incorporation of nucleotides (for example, labeled dNTPs) into template DNA. Such a method for determining an activity is described in, for example, *DNA Polymerase from Escherichia coli,* authored by Richardson C. C., page 264, *Procedures in Nucleic Acids Research,* 1966, published by D. R. Harper & Row Co., Ltd., edited by Cantoni G. L. et al. For example, as to conditions when an activity of Taq DNA polymerase, which is DNA polymerase derived from *Thermus aquaticus* is determined by the method, the following conditions are exemplified.

(a) template DNA: activated salmon sperm DNA;

(b) a composition of a reaction mixture: 25 mM TAPS (pH 9.3 at 25° C.), 50 mM potassium chloride, 2 mM magnesium chloride, 1 mM β-mercaptoethanol, 200 µM each of dATP, dGTP and dTTP, and 100 µM [α-$^{32}$p] dCTP, a total volume of 50 µl;

(c) a method for determining an activity: To a reaction mixture having the composition of (b) containing the template DNA of (a) is added a sample containing Taq DNA polymerase, and the resulting mixture is incubated at 74° C. for 10 minutes. Thereafter, acid-insoluble substances are collected, and the radioactivity contained in the acid-insoluble substances are determined.

Activated salmon sperm DNA used in the above method for determining an activity is prepared as follows.

① Salmon testes DNA (manufactured by Sigma Co., Ltd.) is allowed to swell with sterilized water.

② Seventy units per microliter of DNase I (manufactured by Takara Shuzo Co. Ltd.) is diluted with 150 mM sodium chloride so as to be diluted within a range of 500 times–4000 times, preferably within a range of 1500 times–3000 times.

③ To 20 mg of the above swelled DNA are added 50 mM Tris-hydrochloric acid buffer (pH 7.5), 5 mM magnesium chloride, 0.05% BSA, 50 µl of the above diluted DNase I, so as to make up a volume of 10 ml of a reaction mixture.

④ After treatment at 37° C. for 10 minutes, enzyme is inactivated by treating at 77° C. for 10 minutes. To a partial portion thereof, perchloric acid ($HClO_4$) is added, so as to have a final concentration of about 0.4 M, and the resulting mixture is centrifuged, thereby providing the resulting supernatant as an $A_{260}$ sample. The remaining portion is purified by subjecting it to phenol extraction, chloroform/isoamyl alcohol extraction, and ethanol precipitation.

⑤ Absorbance of $UV_{260}$ of DNA before the above enzyme treatment ($A_{260}$ control) and that of the $A_{260}$ sample obtained in the above item ④ are determined to calculate decomposition rate using ($A_{260}$ sample) /($A_{260}$ control)× 100 (%). In this case, as a substrate for determining the above incorporating activity, there can be used an enzyme-treated DNA having a decomposition rate of preferably from about 3% to about 9%, more preferably about 4.5% to about 7.5%.

Incidentally, depending on the kinds of enzymes to be tested for incorporating activity, it is reasonable to select an enzyme-treated DNA having the most optimal decomposition rate in a preliminary experiment using an enzyme-treated DNA having each decomposition rate.

Usually, one unit (hereinafter described as "1 U") of DNA polymerase activity determined by the above method, namely, an activity for incorporating dNTPs into DNA (hereinafter, simply described as dNTPs-incorporating activity) is defined as "an amount of enzyme capable of incorporating 10 nmol of dNTPs per 30 minutes into acid-insoluble substances".

Conventionally, in PCR using a DNA polymerase, it is standard to add a DNA polymerase in an amount of 1.25 U to 2.5 U as a dNTPs-incorporating activity in 50 µl of a reaction mixture. Although not particularly limited in the present invention, DNA amplification with a short time period conventionally not achieved, namely, speedup of PCR, can be achieved by carrying out PCR with addition of DNA polymerase in an amount of 4 to 20 U as a dNTPs-incorporating activity per 50 µl of a reaction mixture.

An example of rapid PCR of the present invention is shown in Table B. By comparison of Table A with Table B mentioned above, an effect of shortening a time period by the rapid PCR of the present invention is obvious. According to the present invention, there is provided rapid PCR with a shortened total time period for PCR.

TABLE B

Enzyme: Polymerase A
Template DNA: *E. coli* Genomic DNA
[100 ng/50 µl (PCR Reagent Mixture)]

| | | |
|---|---|---|
| Amplification of 1 kbp Fragment | 98° C. 5 sec. 66° C. 2 sec. | 30 cycles (about 20 minutes) |
| Amplification of 10 kbp Fragment | 98° C. 5 sec 68° C. 70 sec. | 30 cycles (about 53 minutes) |
| Amplification of 20 kbp Fragment | 98° C. 5 sec. 68° C. 150 sec. | 30 cycles (about 93 minutes) |

In Table B, as polymerase A, there is used DNA polymerase in an amount of 5 U as a dNTPs-incorporating activity per 50 µl (PCR reagent mixture). In addition, in Table B, *E. coli* genomic DNA is the same as that in Table A.

When the effective amount of DNA polymerase used in the rapid PCR of the present invention is used in amplification of a DNA fragment under conditions for the rapid PCR of the present invention, there is provided an amount of amplified products of the same level as that of carrying out PCR using TaKaRa Ex Taq in an amount of 1.25 U as a dNTPs-incorporating activity per 50 µl as shown in Table A. Therefore, while the activity unit for an effective amount of DNA polymerase used in the present invention shows a higher activity unit in the dNTPs-incorporating activity than that of the prior arts, an activity unit expressed by PCR performance, namely an activity unit expressed by comparison of amounts of amplified products in PCR processes (PCR effective ratio), is of the same level as that of the prior arts.

Embodiments of the DNA synthesis method of the present invention include a method of using one kind of DNA polymerase and a method of using two or more kinds of DNA polymerases. The above method of using two or more kinds of DNA polymerases includes concretely a method of using DNA polymerase having 3'→5' exonuclease activity and the other DNA polymerase substantially having no 3'→5' exonuclease activity (*Proceedings of the National Academy of the Sciences of the USA*, supra); a method of using two or more kinds of DNA polymerases each having 3'→5' exonuclease activity; a method of using α-type DNA polymerase and non-α, non-pol I type DNA polymerase; and the like. Here, "the other DNA polymerase substantially having no 3'→5' exonuclease activity" includes naturally-occurring DNA polymerase having no 3'→5' exonuclease activity or DNA polymerase in which functional portion involved in expression of 3'→5' exonuclease activity is artificially modified to exhibit no activity.

The amount of DNA polymerase used in the present invention (in other words, the above "effective amount of DNA polymerases") is an amount exceeding an amount of DNA polymerase standardly used in the indication "dNTPs-incorporating activity" as described in the instruction manuals, and the like, which are attached to a commercially available enzyme and kit for standard PCR method. Based on this indication of enzyme activity, an effective amount may be used, wherein the effective amount is an amount effective for exhibiting an effect of shortening a time period required in operation.

Concretely, it is desired that the amount of DNA polymerase used in the present invention, in the indication of dNTPs-incorporating activity, is preferably twice or more, more preferably four times or more, the amounts of enzyme used in conventional PCR, from the viewpoint of fully exhibiting the effect of shortening a time period required in operation, and that the amount is preferably 30 times or less, more preferably 20 times or less, the amounts of enzyme used, from the same viewpoint as above. In addition, when two or more kinds of DNA polymerases are used, there may be used an effective amount of each enzyme, or an effective amount as the amount of enzyme for any one of two or more kinds of DNA polymerases. As a result, as shown in the following examples, according to the DNA synthesis method of the present invention, namely rapid PCR, there can be achieved DNA amplification with a short time period, and confirmation of amplified DNA by general agarose electrophoresis, even under such PCR conditions with a shortened time period that amplification of a desired DNA fragment cannot be confirmed by general agarose electrophoresis or the like, when DNA polymerase is used in an amount in the conventional PCR.

The above "effective amount of DNA polymerase" may be determined, for example, as follows. Concretely, regarding to an arbitrary template DNA, PCR is carried out under standard PCR conditions (standard conditions) such as an amount of enzyme, a thermal profile, and the like, which are standardly used for the amplification of the template DNA. Next, an enzyme amount is determined by adjusting a time period for each reaction step under standard conditions; setting PCR conditions so as to shorten a time period required for a whole amplification reaction; thereafter carrying out PCR, with varying amounts of enzyme, wherein the enzyme amount is an amount obtainable in substantially the same level in PCR performance as an amount of amplified products when a standard amount of the enzyme used, so that the enzyme amount determined or an amount not less than the enzyme amount can be defined as an effective amount of DNA polymerase, which is used for the rapid PCR of the present invention. Here, "amount of amplified products" is quantified by, for example, subjecting a given amount of a sample obtained after termination of PCR to electrophoresis; staining the resulting gel after electrophoresis by ethidium bromide to visualize the band ascribed to amplified products; and thereafter measuring fluorescent intensity of the band with the use of instrument, such as an image analysis device (image analyzer) or a densitometer, the instrument being capable of quantifying an amount of a DNA fragment contained in the band which is separated on the gel. Furthermore, an amount of a DNA fragment may be quantified by a known DNA quantification method after purification of amplified products in the sample.

In the rapid PCR of the present invention, the reaction time which is set for each step is not particularly limited, as long as the reaction time is relatively short, as compared to the reaction time under the standard conditions, and exhibits the same level of the enzyme activity as represented by the PCR performance. In the present invention, it is possible to set PCR conditions such that the reaction time for all processes, namely a total time period for PCR is one-half to one-quarter or less of the conventional total time period for PCR. For instance, in the case of amplification of a 1 kbp fragment, while conventional one cycle requires 3 minutes, one cycle in the rapid PCR of the present invention can be shortened to 40 seconds, so that the total time period for PCR is two-ninth of the conventional one. In the case of amplification of a 2 kbp fragment, while conventional one cycle requires about 9 minutes, one cycle in the rapid PCR of the present invention can be shortened to about 1.8 minutes, so that the total time period for PCR is about one-fifth of the conventional one. In the case of amplification of a 10 kbp fragment, while conventional one cycle requires about 16 minutes, one cycle in the rapid PCR of the present invention can be shortened to about 3 minutes, so that the total time period for PCR is about one-fifth of the conventional one.

Conventionally, as enzymes possessing excellent DNA synthesizing speed and capable of amplifying DNA in a short time period, there has been known an enzyme composition comprising DNA polymerase (KOD DNA polymerase) derived from Pyrococcus sp. KOD 1 (Japanese Patent Laid-Open No. Hei 10-42874, trade name: KOD Dash DNA polymerase, manufactured by TOYOBO CO., LTD.). However, no amplified fragments can be visibly confirmed and the amount of the amplified product as quantified by high-sensitive image analyzer is 10 ng or less, even if the enzyme composition were used under the above conditions in a standard amount used of 2.5 U/50 $\mu$l as described in the article of manufacture in accordance with the instruction manual, and thereafter the resulting reaction mixture is subjected to general agarose electrophoresis. On the other hand, when the enzyme is used at an "effective amount of the DNA polymerase" as defined in the present invention, even under the above conditions, amplified fragments can be confirmed by agarose electrophoresis, and the amount of its amplified product is an amount exceeding 10 ng.

The DNA polymerase which can be used for the DNA synthesis method of the present invention (namely the rapid PCR) is not particularly limited, and includes, for instance, pol I-type DNA polymerases (*E. coli* DNA polymerase I, Klenow fragment, Taq DNA polymerase and the like), $\alpha$-type DNA polymerases [$\alpha$-type DNA polymerase derived from the above-mentioned *Pyrococcus furiosus*, DNA polymerase derived from *Thermococcus litralis* (VENT DNA polymerase), DNA polymerase derived from Pyrococcus sp. KOD1 (KOD DNA polymerase), DNA polymerase derived from Pyrococcus sp. GB-D (DEEP VENT DNA polymerase), and the like], and non-$\alpha$, non-pol I type DNA polymerases not belonging to any of these polymerases. Incidentally, each of the pol I type DNA polymerases and $\alpha$-type DNA polymerases refers to a group of enzymes classified by the homology on the amino acid sequences thereof, and the feature on the amino acid sequences is described in *Nucleic Acids Research* 15, 4045–4057 (1991).

In addition, the non-$\alpha$ non-pol I type DNA polymerase includes, for instance, DNA polymerase derived from *Pyrococcus furiosus* disclosed in WO97/24444 Pamphlet.

The DNA polymerase which can be used for the method of the present invention is not limited to a single kind of a DNA polymerase, and two or more kinds of DNA polymerases can be also used as a DNA polymerase composition by, for instance, mixing a DNA polymerase possessing 3'→5' exonuclease activity with another DNA polymerase possessing substantially no 3'→5' exonuclease activity. A mixing ratio of both the enzymes is not particularly limited, and it may be a mixing ratio appropriate for the rapid PCR of the present invention depending upon the kinds of both the enzymes. It may be used in a ratio of the DNA polymerase possessing 3'→5' exonuclease activity to the other DNA polymerase possessing substantially possessing no 3'→5' exonuclease activity in the range of 9:1–1:500. As an example of a polymerase composition thereof, there can be suitably used TaKaRa Ex Taq DNA polymerase (manufactured by Takara Shuzo Co., Ltd.).

Generally in PCR, DNA amplification is carried out by three-step reaction of dissociation (denaturation) of a double stranded template DNA to a single stranded one, annealing of a primer to a single stranded template DNA, and a complementary strand synthesis (extension) from the primer. In addition, DNA amplification is also carried out in a so-called "shuttle PCR" ["PCR Hou Saizensen (PCR Method Frontier)," *"Proteins, Nucleic Acids, Enzymes"* an extra number 41, No. 5, 425–428 (1996)], which is a two-step reaction in which the annealing step of the primer and the extension reaction step among the three-step reactions described above are carried out at the same temperature. In the DNA synthesis method of the present invention, since the time period required for the above extension step can be particularly shortened, in any of the above-mentioned three-step reaction and two-step reaction, the time period required for an entire synthesis reaction can be shortened.

In the DNA synthesis method of the present invention, when the DNA synthesis reaction is carried out, the DNA synthesis can be further efficiently carried out by subjecting to the DNA synthesis reaction in the presence of a substance possessing the action of enhancing the DNA-synthesizing activity owned by the DNA polymerase, namely a substance for achieving higher performance in the rapid PCR.

As one substance for achieving higher performance in the rapid PCR, there is included a substance having electrically negative charges or a salt thereof, particularly an acidic substance or a salt thereof.

PCR is carried out in the presence of an effective amount of the acidic substance and/or a salt thereof, whereby the conditions for speedup can be universalized. In other words, high-performance rapid PCR can be carried out without being affected by the nature of the template (for instance, GC content, or the like). In addition, at least one kind selected from spergualins, degradation products and salts thereof may be selected.

When the rapid PCR of the present invention is carried out, the details on the function of an effective amount of an acidic substance and/or a salt thereof, for instance, an acidic substance having a sugar backbone structure, are unknown. When an effective amount of the DNA polymerase for carrying out the rapid PCR of the present invention is used, since excess DNA polymerase is trapped with the acidic substance during the DNA synthesis reaction, the high-performance rapid PCR can be further achieved by supplying the most appropriate DNA polymerase for PCR to a template DNA by the effects of the acidic substance.

The action of the acidic substance or a salt thereof of enhancing DNA-synthesizing activity can be evaluated by the size of the DNA strand newly synthesized per unit time period or the amount of the amplified products in PCR. In the DNA synthesis method of the present invention, the above-mentioned acidic substance or a salt thereof is used in an amount effective for exhibiting its action. The effective amount can be evaluated by comparing, for instance, the amount of the amplified products in the case where PCR is carried out by using a reaction mixture in which various amounts of the above acidic substance or a salt thereof are added, with the amount of the amplified products in the case where PCR is carried out without adding these substances. The amount of the amplified products can be quantified, for instance, by subjecting a given amount of the reaction mixture after PCR to electrophoresis, staining the gel after electrophoresis by ethidium bromide or the like, and determining the intensity of fluorescence of the band ascribed to the amplified products by using an imaging analyzer or the like.

The acidic substance possessing an action of enhancing DNA-synthesizing activity is not particularly limited. For instance, acidic macromolecular substances such as acidic polysaccharides can be used. In addition, polyglutamates, polyacrylates, polyvinyl sulfates, polystyrene sulfates, and DNAs not serving as a template for a desired DNA synthesis can be also used. Incidentally, in the present specification, the acidic substance also encompasses a salt of the above acidic substances, as long as it possesses an action for enhancing DNA-synthesizing activity. The acidic polysaccharides which can be used in the present invention include, for instance, sulfate group-containing sulfated polysaccharides representatively exemplified by sulfated-fucose-containing polysaccharides, dextran sulfate, carrageenan, heparin, heparan sulfate, rhamnam sulfate, chondroitin sulfate, and dermatan sulfate (chondroitin sulfate B); polyuronic acids such as hyaluronic acid, alginic acid and pectin, and the like. As the above sulfated-fucose-containing polysaccharides, there can be used sulfated-fucose-containing polysaccharide-F or sulfated-fucose-containing polysaccharide-U. Here, the term "sulfated-fucose-containing polysaccharide-F" refers to a sulfated-fucose-containing polysaccharide substantially containing no uronic acid, obtainable from the plant of Phaeophyceae, for instance, by the method disclosed in WO97/26896 Pamphlet, or by the method disclosed in WO97/47208 Pamphlet. In addition, the term "sulfated-fucose-containing polysaccharide-U" refers to a sulfated-fucose-containing polysaccharide containing uronic acid, obtainable by the method described in the above Pamphlets.

The salt of the above acidic substance is not particularly limited, as long as it possesses an action of enhancing DNA-synthesizing activity, and a water-soluble salt is preferable. The water-soluble salt includes, for instance, alkali metal salts such as sodium dextran sulfate, sodium alginate, sodium polyglutaminate, sodium heparin, potassium dextran sulfate and lithium heparin.

The above acidic substance may be, for instance, naturally occurring products, or chemically or enzymatically synthesized products, as long as the acidic substance is a substance keeping the action of enhancing the DNA-synthesizing activity. The above acidic substance may be any of unpurified products containing the same, partially purified products or purified products. Further, the acidic substance may be subjected to an appropriate modification in a range in which an action of enhancing DNA-synthesizing activity is kept. In addition, the acidic substance used in the present invention may be a substance obtained by subjecting it to degradation procedures so that the molecular weight of the above-mentioned acidic substance is in an appropriate form for exhibiting an action of enhancing DNA-syntbesizing activity, or the acidic substance may be a substance obtained by further subjecting the product after the degradation procedures to a fractionation by molecular weight, as long as the acidic substance possesses an action of enhancing DNA-synthesizing activity. In the present invention, an acidic substance having a molecular weight of several thousands or more can be preferably used. Further, these substances can be used alone or in admixture.

The above acidic substance possessing an action of enhancing DNA-synthesizing activity is added for the purpose of efficiently exhibiting an activity of the DNA polymerase, or of keeping its activity in the rapid PCR of the present invention. The amount added can be optimized depending upon the kinds of the acid substances, and the acidic substance may be added at 0.1 ng to 100 μg, preferably at 1 ng to 10 μg, per 50 μl of the reaction mixture. The action of the acidic substance is not particularly limited, and it is considered to be on the bases of holding the DNA polymerase on its molecule, thereby suppressing the non-specific interaction of the DNA polymerase to a template DNA, and of providing an optimal amount of the DNA polymerase for the template DNA. In other words, the DNA synthesis reaction efficiently progresses by optimizing the interaction between the template DNA and the DNA polymerase, the interaction increasing with the progress of the DNA synthesis reaction.

Further, there are exhibited effects that the influences of amplified regions, nucleotide sequences of the primer, and the like are reduced, thereby stably obtaining amplified products.

The DNA polymerase in which the above acidic substance enhances its activity is not particularly limited. For instance, the above acidic substance can be applied to the DNA synthesis method using various DNA polymerases mentioned above.

In the present invention, there may be added and used to a PCR mixture spergualins and/or salts thereof for the purpose of efficiently exhibiting the activity of the DNA polymerase in the rapid PCR of the present invention, or maintaining its activity.

The spergualins possessing an action of enhancing DNA-synthesizing activity are not particularly limited. Examples thereof include a 15-deoxyspergualin compound represented by the following general formula (I):

Gu—(CH$_2$)$_6$—CONHCH(OR)CONH(CH$_2$)$_4$NH—(CH$_2$)$_3$—NH$_2$ (I)

wherein Gu is guanidino group, and R is hydrogen atom or methyl group, or a salt thereof, and the like.

As the above spergualins, for instance, 15-deoxyspergualin, where R of the above general formula (I) is hydrogen atom, or a salt thereof, is preferable.

In addition, the salt of the spergualins may be a salt with an inorganic acid or a salt with an organic acid, as long as the salt is a substance capable of exhibiting an action of enhancing DNA polymerase activity.

Incidentally, the above spergualins are derivatives of spergualin isolated from producing bacteria of the genus Bacillus, which is a substance known to possess anti-tumor activity, immunoenhancement activity, and immunosuppression activity depending upon the kinds of the derivatives (Japanese Patent Laid-Open Nos. Sho 58-62152, Sho 61-129119 and Sho 64-90164). Therefore, these spergualins can be prepared by readily purifying by a known method, or synthesizing by a known method.

A process for preparing the above 15-deoxyspergualin or a salt thereof is disclosed, for instance, in Japanese Examined Patent Publication No. Sho 61-23183 or Example 6 of U.S. Pat. No. 4,603,015, and the like.

The above spergualins may be naturally occurring products or chemically or enzymatically synthesized products, as long as spergualins are a substance keeping an action of enhancing DNA-synthesizing activity. The above spergualins may be any of unpurified products containing the same, partially purified products or purified products. Further, the above spergualins may be subjected to appropriate modifications or a degraded product in a range in which an action of enhancing DNA-synthesizing activity is kept. Further, these substances can be used alone or in admixture.

In the present specification, the degradation product of the spergualins Is not particularly limited, as long as the degradation product is a substance keeping an action of enhancing DNA-synthesizing activity. The degradation product includes, for instance, a substance formed by hydrolyzing the spergualins at room temperature under strongly alkali condition using sodium hydroxide, a substance formed by hydrolyzing the spergualins with heating under weakly alkali conditions such as buffers for PCR, and the like. The substance formed by hydrolysis under each of the above conditions is not particularly limited. When the above 15-deoxyspergualin compound represented by the general formula (I) is used, the substance includes, for instance, a compound represented by the general formula (II):

$$Gu—(CH_2)_6—CONH_2 \quad (II)$$

wherein Gu is the same group as that of the general formula (I);
a compound represented by the general formula (III):

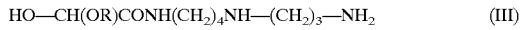

$$HO—CH(OR)CONH(CH_2)_4NH—(CH_2)_3—NH_2 \quad (III)$$

wherein R is the same group as that of the general formula (I);
a compound represented by the general formula (IV):

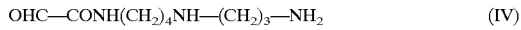

$$OHC—CONH(CH_2)_4NH—(CH_2)_3—NH_2 \quad (IV)$$

and the like. The degradation product of the above spergualins also encompasses a salt of the degradation product of the spergualins, as long as it possesses an action of enhancing DNA-synthesizing activity.

The amount of the above spergualins used is not particularly limited, as long as it is in a range capable of exhibiting an action of enhancing DNA-synthesizing activity. The amount used may be an amount so as to have an optimal concentration depending upon the kinds and amounts of the template DNA used, the length of a region to be amplified, and the kinds of the DNA polymerases. For instance, in the case of 15-deoxyspergualin trihydrochloride, it may be added so as to have a final concentration of 0.1 $\mu$M to 500 $\mu$M, preferably 20 $\mu$M to 100 $\mu$M.

The action of the spergualins of the present invention is not particularly limited, and it is thought to efficiently exhibit the activity of the DNA polymerase or to hold the DNA polymerase, thereby suppressing nonspecific interaction of the enzyme to the DNA. Also, it is thought to act to the complex of template DNA and the primer, thereby facilitating the primer extension reaction.

When the above spergualins and the acidic substance are used in combination, both parties may react to form a salt, and it may be a substance possessing an action of enhancing DNA-synthesizing activity.

When the above spergualins and the acidic substance are used in combination, although there are no particular limitations in the amount, as long as the amount is in a range capable of exhibiting an action of enhancing DNA-synthesizing activity, it may be an amount so as to have optimal coexisting ratio depending upon the kinds and amounts of the template DNA used, the length of a region to be amplified, the kinds of the DNA polymerases, and the like.

Incidentally, the above spergualins or a salt thereof, and a mixture comprising the above substance having electrically negative charges or a salt thereof and the above spergualins or a salt thereof can be used as DNA-synthesizing activity enhancers.

Regarding the DNA synthesis method described above, the method of the present invention also encompasses the detail description of the method, for instance, a method for preparing a PCR reagent mixture, a provision of printed matters describing information such as recommended reaction conditions and an act of instructing the method of the present invention through electronic media such as internet.

(2) Kit Usable for DNA Synthesis Method of Present Invention

Rapid PCR can be carried out by using the kit of the present invention. The kit as mentioned above is not particularly limited, as long as it is a kit usable in the reaction with the DNA synthesis by PCR method, and includes a kit for rapid PCR for carrying out in vitro DNA synthesis reaction.

The kit of the present invention is a kit usable in in vitro DNA synthesis, wherein the PCR reagent mixture prepared in accordance with the instruction of the kit comprises "an effective amount of the DNA polymerase" used in the DNA synthesis method described in item (1) above, i.e. an effective amount of a DNA polymerase such that an amount of a DNA fragment of about 2 kb is more than 10 ng per 50 vl of a reaction mixture, when 35 cycles of PCR is carried out by using 50 $\mu$l volume of a reaction mixture containing 1 ng of E. coli genomic DNA, and 10 pmol each of primers Eco-1 and Eco-2, wherein one cycle consists of 99° C., 1 second–66° C., 7 seconds.

The PCR reagent mixture prepared by using the kit of the present invention is not particularly limited, and for instance, the reagent mixture comprises 4 to 10 U as dNTPs-incorporating activity of a DNA polymerase for rapid PCR in 50 $\mu$l of the reaction mixture, including, for instance, TaKaRa EX Taq DNA polymerase. In addition, as the composition for the reaction mixture, a reagent mixture having a composition appropriate for the DNA polymerase used may be used.

The above "instruction" refers to a printed matter describing a method of use of the kit, for instance, a method for preparing a PCR reagent mixture, recommended reaction conditions, and the like, which may take a form, beside's pamphlet or leaflet type of instruction manuals, of a label attached to the kit, a packaging material enclosing the kit, and the like. Further, it also encompasses information disclosed or provided through electronic media such as internet. Regarding the preparation of the PCR reagent mixture, the kit of the present invention encompasses a kit to which instructions for the use of the amount of the above DNA polymerase and/or the addition of the above acidic substance or a salt thereof are attached, or a kit for which the method of the present invention is disclosed and provided through electronic media such as internet.

In addition, the kit may contain an acidic substance or a salt thereof possessing an action of enhancing DNA-synthesizing activity of the DNA polymerase. As the acidic substance or a salt thereof, ones described in item (1) above can be used. The acidic substance or a salt thereof as mentioned above efficiently allows to exhibit the DNA polymerase activity or to hold the enzyme, whereby the interaction between the DNA and the enzyme can be properly regulated. Therefore, the performance of the kit of the present invention is further improved.

In addition, the kit may comprise at least one kind selected from the group consisting of spergualins, degradation products thereof, and salts thereof.

When the above spergualins and the acidic substance are used in combination, the both parties may react to form a salt, and they may be in any forms as long as they are substances possessing an action of enhancing DNA-synthesizing activity.

The DNA polymerase included in the present invention is not particularly limited, and includes various kinds of DNA polymerases for rapid PCR shown in item (I) above.

The kit may comprise a reagent necessary for the reaction of the DNA polymerase such as dNTPs, magnesium chloride, and buffer components for keeping the reaction mixture at an appropriate pH. The above DNA polymerase, the acidic substance and other reagents may be contained in the kit in a state where each is present as an independent component, or a state in which some of the components are combined, including, for instance, a state in which the components are added to the reaction buffer and the like.

One embodiment of the kit of the present invention includes a composition comprising, besides the above DNA polymerase, various components necessary for DNA synthesis by PCR method, including, for instance, dNTP, magnesium chloride, buffer components for keeping the reaction mixture at an appropriate pH, and the like. The composition may further comprise the above acidic substance. The composition described above can be prepared by adding a primer for amplifying a desired DNA fragment and template DNA, and further adding, as occasion demands, water or buffer, whereby a reaction mixture can be prepared. Furthermore, when the DNA fragment to be amplified by the kit is determined, the composition may comprise a primer appropriate for the amplification of the fragment. By the use of the composition described above, the DNA synthesis reaction, namely the rapid PCR, can be extremely conveniently and rapidly carried out.

When applied to manipulations such as PCR and sequencing utilizing PCR, DNA labeling, cDNA synthesis, and site-directed mutagenesis, the kit of the present invention exhibits an excellent effect that the time period required for the manipulations can be shortened. For instance, when the above kit is applied to PCR, the time period required for amplification of DNA of the same chain length is shorter than that by conventional PCR method or LA-PCR method. Therefore, even under rapid PCR conditions where the amplification of DNA was impossible in the conventional method, the amplification of DNA can be carried out. In addition, since the kit of the present invention can shorten the time period required for the entire amplification reaction, there is exhibited an excellent effect that gene diagnostic method or the like can be carried out at a shorter time period by the use of the gene diagnostic method on the basis of PCR method.

(3) Article of Manufacture of Rapid PCR Agent of the Present Invention

The article of manufacture of a PCR agent of the present invention is an article of manufacture of a PCR agent, comprising packaging material and a PCR reagent contained within the packaging material, wherein the PCR agent comprises DNA polymerases, and wherein a label or instruction indicates that the PCR reagent can be used for PCR in a short time period, the label being attached to the packaging material, and the instruction being enclosed with the packaging material. The above PCR agent may comprise a DNA polymerase and buffer appropriate for the DNA polymerase and/or dNTP. Therefore, one of ordinary skill in the art can conveniently carry out the rapid PCR of the present invention by following the label indicated on the article of manufacture or the instruction manual attached to the manufacture, and the article of manufacture s useful in various industrial fields requiring the rapid PCR of the present invention.

According to the DNA synthesis method (rapid PCR) of the present invention, the time period required for the entire amplification reaction can be shortened. Although it depends upon the performance of the apparatus used, for instance, a total time period for PCR required for amplifying a DNA of 2 kb is shortened to about one-half that of conventional method, and a total time period for amplifying a DNA of about 20 kb is shortened to about one-fifth that of conventional method, whereby speed-up of PCR can be achieved for the first time. The method of the present invention exhibits an excellent effect that gene diagnostic method can be carried out in a shorter period of time by, for instance, the use of gene diagnostic method on the basis of PCR method. The method is particularly suitable for nested PCR or the like in which PCR is carried out twice.

The rapid PCR of the present invention is extremely useful in the development and manufacture of the techniques requiring a large amount of PCR manipulations such as a DNA chip. The DNA chip comprises a glass chip of a size of thumb and about 10000 kinds of DNAs, wherein the DNAs are immobilized on the glass chip. In order to manufacture the DNA chip, it is necessary that DNAs requiring spots are amplified and prepared by amplification with PCR, and the necessary PCR manipulations therefor would be enormous. For instance, if 10000 of DNA chips described above are supposedly made, there is exhibited an effect that the chips can be manufactured in a short time period of about 3 weeks according to the rapid PCR of the present invention, in contrast to an overall period of about 3 months just for PCR manipulations when the conventional PCR is employed.

In addition, the PCR manipulations required for elucidating an entire sequence of genome of *Bacillus subtilis* (5000000 bases) can be achieved in about 3 weeks according to the rapid PCR of the present invention, in contrast to about 3.5 months in the conventional PCR, thereby showing a great difference.

In the rapid PCR of the present invention, PCR can be carried out by using conventional PCR apparatus without using specialized apparatus. The rapid PCR of the present invention is excellent in the rapidness and the reactivity, and is an extremely useful technique as high-sensitivity PCR.

The present invention will be hereinbelow described in further detail by means of the working examples, without intending to restrict the scope of the present invention to these working examples.

In the following working examples, the activities of the commercially available DNA polymerases were represented on the basis of the indicated units in "dNTPs-incorporating activity" described in instruction manual for each enzyme product. In addition, unless specified otherwise, the reaction solution comprising a commercially available enzyme was prepared in accordance with the manual for each enzyme, or prepared by using a reaction buffer attached thereto. PCR was carried out by using TaKaRa PCR Thermal Cycler PERSONAL (manufactured by Takara Shuzo Co., Ltd.) unless specified otherwise.

EXAMPLE 1

(1) Preparation of Primers

Nine kinds of primers λ1 to λ5 and λ7 to λ10 were synthesized on the basis of the nucleotide sequences of λDNA. The nucleotide sequences for the primers λ1 to λ5 and λ8 to λ10 are respectively shown in SEQ ID NOs: 1 to 8 of Sequence Listing. Further, the nucleotide sequence for λ7 is shown in SEQ ID NO: 9 of Sequence Listing. The sizes of DNA fragments amplified by PCR with λDNA as a template depending upon the combinations of these primers are shown in Table 1.

TABLE 1

| Primer Pair | Size of Amplified DNA Fragment |
|---|---|
| λ1/λ2 | 0.5 kb |
| λ1/λ3 | 1 kb |
| λ1/λ4 | 2 kb |
| λ1/λ5 | 4 kb |
| λ1/λ7 | 8 kb |
| λ1/λ8 | 10 kb |
| λ1/λ9 | 12 kb |
| λ1/λ10 | 15 kb |

(2) Preparation of Polymerase A and Polymerase B

Using TaKaRa EX Taq DNA polymerase having a concentration of 5 /µl, its concentrated preparation was prepared. Each of a preparation having a concentration of 10 U/µl (referred to as "Polymerase A") and a preparation having a concentration of 20 U/ µl (referred to as "Polymerase B") was prepared to use in the subsequent examples.

(3) Rapid PCR Using Polymerase A and Polymerase B

According to the instruction manual attached to TaKaRa EX Taq DNA polymerase, the DNA polymerase is usually used in an amount of 1.25 U per 50 µl of a PCR reagent mixture. In this example, rapid PCR was studied by varying the amount of each of the DNA polymerases.

PCR was carried out by preparing a PCR reagent mixture comprising λDNA as a template, and primers λ1 and λ4 as a primer pair. The composition of the PCR reagent mixture is shown below.

Composition of PCR Reagent Mixture 50 mM Tris-acetate (pH 8.5), 0.2 mM each of dATP, dCTP, dGTP and dTTP, 3 mM magnesium acetate, 50 mM potassium acetate, 1 pg of λDNA, 10 pmol each of primers λ1 and λ4. To the above PCR reagent mixture were added 1.25 U of TaKaRa EX Taq DNA polymerase and 0.5 λl of Polymerase A or 0.5 µl of Polymerase B, each mixture making up a final volume of 50 µl.

Rapid PCR was carried out in 35 cycles for a total time period of about 31.5 minutes, wherein one cycle of reaction comprises a process consisting of 98° C., 5 seconds–66° C., 10 seconds. After the termination of reaction, 5 µl of the resulting sample was electrophoresed on 1% agarose gel containing ethidium bromide in an amount of 0.00005%, thereby confirming a desired amplified fragment of about 2 kb. The results thereof are shown in Table 2.

TABLE 2

| Enzyme Used | Amplification Results |
|---|---|
| 1.25 U/50 µl of PCR TaKaRa EX Taq | − |
| Polymerase A | ++ |
| Polymerase B | ++ |

++: Intensive amplification being observed;
+: Amplification being observed;
±: Slight amplification being observed; and
−: No amplification being observed.

As shown in Table 2, there could be confirmed that rapid PCR can be carried out by using Polymerase A [5 U/50 µl (PCR reagent mixture)] or Polymerase B [10 U/50 µl (PCR reagent mixture)].

EXAMPLE 2

(1) Preparation of Primers

Five kinds of primers Eco1, Eco-2, Eco-2-2, Eco-5 and Eco-6 were synthesized on the basis of the nucleotide sequence of *E. coli* genomic DNA. The nucleotide sequences of the primers Eco-1, Eco-2, Eco-2-2, Eco-5 and Eco-6 are respectively shown in SEQ ID NOs: 10 to 14 of Sequence Listing. The sizes of DNA fragments depending upon the combinations of these primers are shown in Table 3 being amplified by PCR with *E. coli* DNA as a template.

TABLE 3

| Primer Pair | Size (kb) of Amplified DNA Fragment |
|---|---|
| Eco-1/Eco-2 | 2 |
| Eco-2-2/Eco-5 | 8 |
| Eco-1/Eco-6 | 20 |

(2) Rapid PCR When Polymerase A Was Used

Rapid PCR using Polymerase A was studied. Rapid PCR was carried out by preparing a PCR reagent mixture containing each of the combinations of primers Eco-1 and Eco-2, primers Eco-2-2 and Eco-5, and primers Eco-1 and Eco-6 as a primer pair using as a template *E. coli* genomic DNA in genome DNA set (manufactured by Takara Shuzo Co., Ltd.) for LA PCR™. The composition of the PCR reagent mixture is shown below.

Composition of PCR Reagent Mixture 50 mM Tris-acetate (pH 8.5), 0.2 mM each of dATP, dCTP, dGTP and dTTP, 3 mM magnesium acetate, 50 mM potassium acetate, 10 pmol each of the combinations of primers Eco-1 and Eco-2, primers Eco-2-2 and Eco-5, and primers Eco-1 and Eco-6. Incidentally, when the size of the fragment to be amplified are 2 kb and 8 kb, 1 ng of *E. coli* genomic DNA was used, or when the size was 20 kb, 20 ng of *E. coli* genomic DNA was used. To the above PCR reagent mixture were added 0.5 μl of Polymerase A and 2.5 μg of sodium alginate, each making up a final volume of 50 μl.

PCR was carried out in a fast mode under temperature conditions as shown in Table 4 by using TaKaRa PCR Thermal Cycler PERSONAL (manufactured by Takara Shuzo Co., Ltd.). After the termination of reaction, 5 μl of each resulting sample was electrophoresed on 1% agarose gel containing ethidium bromide in an amount of 0.00005%, thereby confirming an amplified fragment. The results thereof are shown in Table 4.

TABLE 4

| | PCR | | | |
| --- | --- | --- | --- | --- |
| Size (kb) of Amplified DNA Fragment | Reaction Temp. Conditions (1 Cycle) | Number of Cycles | Total Period of Time (minute) | Amplification Results Polymerase A |
| 2 | 99° C./1 s, 66° C./6 s | 35 | About 25.1 | + |
| | 99° C./1 s, 66° C./7 s | 35 | About 25.7 | ++ |
| | 99° C./1 s, 66° C./8 s | 35 | About 26.3 | +++ |
| 8 | 99° C./1 s, 68° C./60 s | 35 | About 56.6 | + |
| | 99° C./1 s, 68° C./70 s | 35 | About 62.4 | +++ |
| | 99° C./1 s, 68° C./80 s | 35 | About 68.3 | ++++ |
| 20 | 99° C./1 s, 68° C./150 s | 35 | About 108.5 | ++ |
| | 99° C./1 s, 68° C./165 s | 35 | About 117.3 | +++ |

+ to ++++: Extent of amplification is shown in 4 grades.
−: No amplification being observed.

As shown in Table 4, when Polymerase A was used, there was confirmed that a fragment of 2 kb, 8 kb or 20 kb was amplified which was anticipated under any of rapid PCR conditions. Further, when similar PCR was carried out with 0.5 μl of Polymerase B, there was found to have the same results as in Polymerase A.

(3) Comparison with DNA Polymerases Marketed by Other Manufacturers

Among the rapid PCR experiments shown in Item (2) of Example 2, with respect to a product experiments allowing to amplify a DNA fragment of 2 kb, its amount of amplified fragment was quantified. As a control, KOD dash DNA Polymerase (manufactured by TOYOBO CO., LTD.) was used. With respect to KOD dash DNA Polymerase, there were quantified an amount of amplified fragment, with a PCR reagent mixture having an amount of used enzyme of 2.5 U, a standard unit amount of the used enzyme described in its instruction manual, per 50 μl of the PCR reagent mixture, and also with each of PCR reagent mixtures having the unit amount increased to 5 U or 10 U.

Rapid PCR was carried out in 35 cycles, wherein one cycle comprises a process consisting of 99° C., 1 second–66° C., 7 seconds. PCR was carried out in a fast mode by using TaKaRa PCR Thermal Cycler PERSONAL (manufactured by Takara Shuzo Co., Ltd.). The standard values in the fast mode of Thermal Cycler are shown in Table 5.

TABLE 5

| | Definition of Standard Value | Standard Value |
| --- | --- | --- |
| Heat rate | Maximum heating rate when heating from 35° to 94° C. | ≧1.5° C./s |
| Cool rate | Maximum cooling rate when cooling from 94° to 40° C. | ≧1.5° C./s |
| Over temp | Indicating how many degrees block temperature is raised from the set temperature and then stabilized | ≦1.0° C. |
| Under temp | Indicating how many degrees block temperature is lowered from the set temperature and then stabilized | ≦2.0° C. |

When the temperature conditions were set as described above, a step of one cycle required about 45 seconds, and a total time period of PCR was about 25.7 minutes. Eight microliters of each sample after termination of reaction was electrophoresed on 1% agarose gel containing ethidium bromide in an amount of 0.00005%, thereby confirming an amplified fragment. As a result, when Polymerase A and 5 U and 10 U of KOD dash DNA Polymerase were used, a desired amplified fragment of about 2 kb could be confirmed. On the other hand, when 2.5 U of KOD dash DNA Polymerase was used, a desired amplified fragment could not be confirmed. Therefore, a desired amplified fragment was detected and quantified by using an image analyzer FM-BIO (manufactured by Takara Shuzo Co., Ltd.) having a further enhanced detection sensitivity, with a DNA molecular weight marker at a known amount as a control, while adjusting the detection sensitivity. As a result, there could be confirmed a slight amplification even in 2.5 U of KOD dash DNA Polymerase. The quantified values are shown in Table 6.

TABLE 6

| Used Enzyme | Quantified Value (ng) |
| --- | --- |
| Polymerase A | 153 |
| 2.5 U KOD dash | ≦10 |
| 5 U KOD dash | 28 |
| 10 U KOD dash | 88 |

As shown in Table 6, in the quantification by the image analyzer, the amount of amplified DNA when Polymerase A was used was about 153 ng, per 50 μl of the sample after the reaction.

On the other hand, in the quantification by the image analyzer, even in the case of KOD dash DNA polymerase, an amplified product of an amount more than 10 ng could not be obtained in a standard used amount [2.5 U/50 μl (PCR reagent mixture)] described in its instruction manual. However, when the amount of used enzyme was doubled or quadrupled, 28 ng and 88 ng of amplified products, respectively, were obtained. In other words, not only in Polymerase A but also in KOD dash DNA polymerase, the amount of amplified DNA was increased by increasing its amount. In addition, a PCR reagent mixture was prepared from the PCR reagent mixture for Polymerase A used in Item (2) of Example 2 without adding sodium alginate. When rapid PCR was carried out under the above reaction conditions and by using the PCR reagent mixture using Polymerase A, there was confirmed that an amplified fragment of the amount more than 10 ng was obtained.

Therefore, under the above conditions, amplified fragments could be visually confirmed by general agarose electrophoresis, regardless of the kinds of the DNA polymerases, by using an amount of DNA polymerase capable of obtaining an amplified product of an amount more than 10 ng. Therefore, it was clarified that rapid PCR of which amount of the resulting amplified product was more than 10 ng could be carried out.

EXAMPLE 3

A total time period of PCR in rapid PCR, the time period being required for obtaining the same amount of the amplified product using Polymerase A, was studied for 3 kinds of commercially available thermal cyclers on the basis of basic protocol conditions using TaKaRa EX Taq DNA polymerase in an amount of 1.25 U/50 μl (PCR reagent mixture) as described in the instruction manual for TaKaRa EX Taq DNA polymerase. The basic protocol conditions were set by referring to conditions described at page 6 of TaKaRa *PCR Enzymes* (published by Takara Shuzo Co., Ltd., May Edition, 1998) when amplifying a fragment of 20 kb; or to conditions for TaKaRa LA Taq DNA polymerase described at page 8 of the manual attached to TaKaRa LA PCR Kit Ver. 2.1 (manufactured by Takara Shuzo Co., Ltd.) when amplifying fragments of a size other than the above. As the thermal cyclers, there were used 3 equipments, namely TaKaRa PCR Thermal Cycler MP (manufactured by Takara Shuzo Co., Ltd.; referred to as "MP" in Table 7); TaKaRa PCR Thermal Cycler PERSONAL (manufactured by Takara Shuzo Co., Ltd.; referred to as "PP" in Table 7); and GeneAmp PCR System 9600 (manufactured by Perkin-Elmer; referred to as "9600" in Table 7").

TABLE 7

| Size (kb) of Amplified DNA Fragment | Equipments Used | Temperature Conditions for One Cycle (Upper Row) [Total Period of Time for PCR] (Lower Row) | |
|---|---|---|---|
| | | 1.25 U/50 μl (PCR Reagent Mixture) TaKaRa EX Taq | Polymerase A |
| 2 | PP | 98° C./10 s, 68° C./60 s [About 58 min]. | 98° C./5 s, 66° C./10 s [About 27 min.] |
| | MP | 98° C./10 s, 68° C./60 s [About 67 min] | 98° C./1 s, 66° C./10 s [About 37 min.] |
| | 9600 | 98° C./10 s, 68° C./60 s [About 70 min.] | 98° C./1 s, 66° C./10 s [About 36 min.] |
| 8 | PP | 98° C./10 s, 68° C./5 min. [About 178 min.] | 98° C./5 s, 68° C./75 s [About 58 min.] |
| | MP | 98° C./10 s, 68° C./5 min. [About 187 min.] | 98° C./1 s, 68° C./75 s [About 69 min.] |
| | 9600 | 98° C./10 s, 68° C./5 min. [About 190 min] | 98° C./1 s, 68° C./75 s [About 67 min.] |
| 20 | PP | 98° C./10 s, 68° C./15 min. [About 478 min.] | 98° C./5 s, 68° C./3 min. [About 110 min.] |
| | MP | 98° C./10 s, 68° C./15 min. [About 487 min.] | 98° C./1 s, 68° C./3 min. [About 121 min.] |
| | 9600 | 98° C./10 s, 68° C./15 min. [About 490 min.] | 98° C./1 s, 68° C./3 min. [About 119 min.] |

The kinds of the template used, the amount of the template, the primer pair, the amount of the enzyme and the composition for the PCR reagent mixture were made to be the same as those in Example 2. PCR was carried out for 30 cycles under each of the conditions listed in Table 7, and thereafter the amounts of the amplified products were quantified by the method described in Item (3) of Example 2. Incidentally, TaKaRa PCR Thermal Cycler PERSONAL was set at normal mode when using 1.25 U, and set at fast mode when using Polymerase A.

As a result, differences in the amounts of the amplified products obtained under each of conditions using TaKaRa EX Taq DNA polymerase in an amount of 1.25 U/50 μl (PCR Reagent Mixture) and Polymerase A were not found. In other words, the enzyme activity indicated by each PCR performance was of the same level. On the other hand, it has been shown from the results of Table 7 that a time period required for an entire amplification reaction, namely, a total time period of PCR, is markedly shortened to about ½ to about ⅕ by using Polymerase A. Thus, it has been shown that rapid PCR could be carried out. From the above, when an effective amount of the DNA polymerase of the present invention was used, it was shown that even with the shortened set time period, an amplification ratio per one cycle was of the same level to that under standard reaction conditions. Incidentally, as a control, PCR was carried out under the reaction conditions used for Polymerase A mentioned above by using TaKaRa EX Taq DNA polymerase in an amount of 1.25 U/50 μl (PCR Reagent Mixture). As a result, no amplification could be confirmed in any of the primer pairs used.

EXAMPLE 4

Comparison of the amounts of amplified products was made when PCR was carried out using TaKaRa Taq DNA polymerase and Polymerase A under reaction conditions appropriate for each polymerase. An amount of a product of about 500 bp resulting from amplification with λDNA as a template and primers λ1 and λ2 as the primer pair was used as an index.

a) TaKaRa Taq DNA Polymerase Reaction System: A PCR reagent mixture having a final volume of 50 μl comprising 1 ng or 100 pg of λDNA, 10 pmol each of primers λ1 and λ2, 1.25 U of TaKaRa Taq DNA polymerase, and DATP, dCTP, dGTP and dTTP each at a final concentration of 0.2 mM was prepared by using TaKaRa PCR Amplification Kit and using the attached reaction buffer in accordance with the instruction manual for the kit. PCR System 9600 was used as the thermal cycler. PCR was carried out in 25 cycles, wherein one cycle comprises a process consisting of 94° C., 30 seconds–55° C, 30 seconds–72° C., 30 seconds, one cycle being set at about 167 seconds. After termination of the reaction, 8 μl of each sample was electrophoresed on 1% agarose gel containing ethidium bromide in an amount of 0.00005%, thereby confirming an amplified fragment. Further, an amount of an amplified fragment was quantified with a DNA molecular weight marker at a known amount as a control, with adjusting the detection sensitivity by using an image analyzer FM-BIO.

b) Polymerase A Reaction System: A PCR reagent mixture having a final volume of 50 μl comprising 50 mM Tris-acetate (pH 8.5), 0.2 mM each of DATP, dCTP, dGTP and dTTP, 3 mM magnesium acetate, 50 mM potassium acetate, 1 ng or 100 pg of λDNA, 10 pmol each of primers λ1 and λ2, 0.5 μl of Polymerase A and 2.5 μg of sodium alginate was prepared. PCR System 9600 was used as the thermal cycler. PCR was carried out in 25 cycles, wherein one cycle comprises a process consisting of 98° C., 5 seconds–55° C., 5 seconds–72° C., 5 seconds. Eight microliters of the sample after termination of the reaction was electrophoresed on 1% agarose gel containing ethidium bromide in an amount of 0.00005%, thereby confirming an amplified fragment. Further, an amplified fragment was quantified with a DNA molecular weight marker at a known amount as a control, with adjusting the detection sensitivity by using an image analyzer FM-BIO. The quantified value was compared with the quantified value of the amplified product obtained for the TaKaRa Taq DNA polymerase having a concentration of 1.25 U.

As a result, the amount of the amplified product was larger in a case where 1 ng of λDNA was used as a template for either of the enzymes used. In addition, there was found no differences in the amounts of the amplified products for the same amount of the template between TaKaRa Taq DNA polymerase and Polymerase A, showing that substantially the same amount of the DNA fragment was amplified for both PCRs. In other words, the enzyme activity represented by PCR performance was of the same level for both PCRs. Therefore, in a reaction consisting of the same number of cycles, while the extension reaction time in the TaKaRa Taq DNA polymerase system was 30 seconds at 72° C., the extension reaction of 5 seconds at 72° C. was enough in the Polymerase A Reaction System.

In other words, there could be confirmed that rapid PCR could be carried out in which about 167 seconds per one cycle in a convention process was shortened to about 92 seconds per one cycle, a total time period of PCR being shortened to about ½.

EXAMPLE 5

Enhancement of Tag DNA Polymerase-Synthesizing Activity by Acidic Substance (1) Preparation of Sulfated-Fucose-Containing Polysaccharide-F The sulfated-fucose-containing polysaccharide-F used in the subsequent examples was purified by the following process. A preparation example of sulfated-fucose-containing polysaccharide-F is given hereinbelow.

Gagome seaweed was sufficiently dried, and thereafter 20 kg, a weight on a dry basis, of the Gagome seaweed was pulverized. Next, the resulting dry powder was suspended in 900 liters of tap water containing 7.3 kg of calcium chloride•dihydrate, and the temperature was raised to 90° C. over a period of 40 minutes with stirring. The extraction was carried out for one hour with keeping at 90° to 95° C. Thereafter, the resulting solution was cooled to 20° C., stopped stirring, and allowed to stand overnight, to give an extract.

Next, solid-liquid separation was carried out using a centrifuge (Model CNA, manufactured by Westfalia Separator Inc.). About 900 liters of supernatant of the solid-liquid separation was obtained from the above extract by using the centrifuge. Three-hundred and sixty liters of the supernatant was filtered with SPARKLER FILTER (manufactured by Nippon Senshoku Kikai) incorporated with a filter of a size of 3 μm (manufactured by Nippon Shokuhin Rozai). The filtrate was concentrated to a volume of 20 liters by an UF membrane ("FE10-FC-FUS0382," manufactured by DAICEL CHEMICAL INDUSTRIES, LTD.) having a fractionated molecular weight of 30000. Thereafter, 20 liters of tap water was added to the resulting concentrate, and the dilution was concentrated again to a volume of 20 liters. The dilution-concentration procedures as described above were repeated five time, to give 25 liters of a concentrate.

To 700 ml of the above concentrate were added so as to give a final concentration of 0.2 M calcium chloride and 20 mM sodium acetate. Thereafter, the resulting mixture was dialyzed against 20 mM sodium acetate equilibrated buffer (pH 6.0) containing 0.2 M calcium chloride. The solution after the dialysis treatment was applied to 3500 ml of DEAE-Sepharose FF column (column inner diameter: 9.7 cm) equilibrated with 10 liters of the above equilibrated buffer, and washed with 5 liters of the equilibrated buffer. The elution was carried out under 3-step gradient conditions given hereinbelow.

Incidentally, the flow rate of the chromatography was set at 3500 ml/1 hour.

Gradient Conditions

1] linear gradient of 0 to 0.5 M sodium chloride (amount of eluent: 4.5 liters)
2] linear gradient of 0.5 to 1.0 M sodium chloride (amount of eluent: 4.5 liters)
3] linear gradient of 1.0 to 2.0 M sodium chloride (amount of eluent: 4.5 liters)

The eluent was collected 250 ml per one fraction. Each fraction was subjected to sugar quantification by phenol sulfuric acid method, and to uronic acid quantification by carbazole-sulfuric acid method. As a result, fractions of Fraction Nos. 40 to 53, which were fractions having high sugar contents and low contents of uronic acid, were obtained. The fractions of Fraction Nos. 40 to 53 are referred to "sulfated-fucose-containing polysaccharide-F fractions." Each of the sulfated-fucose-containing polysaccharide-F fractions was concentrated with a ultrafiltration membrane of 100000, and thereafter the concentrate was dialyzed against 50 mM sodium citrate, and further dialyzed overnight against distilled water. Subsequently, the mixture was lyophilized, to give 1.696 g of sulfated-fucose-containing polysaccharide-F from the sulfated-fucose-containing polysaccharide-F fraction.

(2) Effects of Acidic Substance Against Taq DNA Polymerase

Using as acidic substances the sulfated-fucose-containing polysaccharide-F obtained by the process described in Item (1) of Example 5, dextran sulfate powder (manufactured by Onco), or sodium alginate (100 to 150 centipoises, manufactured by Wako Pure Chemicals), the effects of these acidic substances on the activity of TaKaRa Taq DNA polymerase (manufactured by Takara Shuzo Co., Ltd.) were examined.

A PCR reagent mixture comprising λDNA as a template, primers λ1 and λ7 as a primer pair and TaKaRa Taq DNA polymerase as a DNA polymerase was prepared, and PCR was carried out. The PCR reagent mixture was prepared so as to have the following composition.

Composition of PCR Reagent Mixture

Buffer for TaKaRa Taq DNA polymerase, 10 U of TaKaRa Taq DNA polymerase, 100 pg of λDNA, 0.2 mM each of DATP, dCTP, dGTP and dTTP, and 5 pmol each of primers λ1 and λ7 (final volume being 25 μl). Further, 0.25 ng of the sulfated-fucose-containing polysaccharide-F, 0.25 ng of dextran sulfate powder, or 0.5 μg of sodium alginate were added as acidic substances to the above PCR reagent mixture.

The reaction was carried out in 30 cycles for a total time period of PCR of about 110 minutes, wherein one cycle of reaction comprises a process consisting of 98° C., 5 seconds–68° C., 3 minutes. After the termination of reaction, 5 μl of the resulting sample was electrophoresed on 1% agarose gel containing ethidium bromide in an amount of 0.00005%, thereby confirming an amplified fragment. The results thereof are shown in Table 8.

TABLE 8

| Acidic Substance | Amount Added | Amplification Results |
|---|---|---|
| Sulfated-Fucose-Containing Polysaccharide-F | 0.25 ng | ++ |
| Dextran Sulfate Powder | 0.25 ng | ++ |
| Sodium Alginate | 0.5 µg | ++ |
| No Addition | | ± |

++: Intensive amplification being observed;
+: Amplification being observed;
±: Slight amplification being observed; and
−: No amplification being observed.

As shown in Table 8, there was confirmed that an expected 8 kb fragment was excellently amplified in case where any kinds of acidic substances were added, and thus rapid PCR could be carried out. Incidentally, in this Example, when template DNA was increased from 100 pg to 1 ng, the amount of a desired amplified product was improved even in a case of no addition of the acidic substance. On the other hand, even when the reaction was carried out under the above PCR conditions by using 1.25 U of TaKaRa Taq DNA polymerase and 1 ng of template DNA, a desired amplified product could not be obtained. By adding the acidic substance, it was shown that rapid PCR of an even higher performance could be carried out.

EXAMPLE 6

Rapid PCR by Combination of DNA Polymerase for LA-PCR with Acidic Substance

Rapid PCR in the presence of the acidic substances was studied in LA-PCR using a combination of a DNA polymerase having 3'→5' exonuclease activity and a DNA polymerase without having the activity.
(1) Rapid PCR by Combination of Polymerase A with Acidic Substance Using λDNA as template, a PCR reagent mixture comprising λDNA as a template, primers λ1 and λ8 as a primer pair was prepared, and PCR was carried out. The composition for a PCR reagent mixture is as follows.

Composition of PCR Reagent Mixture 50 mM Tris-acetate (pH 8.5), 0.2 mM each of dATP, dCTP, dGTP and dTTP, 3 mM magnesium acetate, 50 mM potassium acetate, 10 pg of λDNA, 0.5 µl of Polymerase A and 10 pmol each of primers λ1 and λ8 (final volume being 25 µl). Further, 2.5 µg of sodium alginate was added to the above PCR reagent mixture. As a control, a PCR reagent mixture without adding sodium alginate was also prepared.

Reaction Conditions: The reaction was carried out in 30 cycles, wherein one cycle of reaction comprises a process consisting of 98° C., 5 seconds–68° C., 75 seconds. The reaction was carried out in fast mode using TaKaRa PCR Thermal Cycler PERSONAL (manufactured by Takara Shuzo Co., Ltd.).

After the termination of reaction, 6 µl each of the resulting sample was electrophoresed on 1% agarose gel containing ethidium bromide in an amount of 0.00005%, thereby confirming an amplified fragment of about 10 kb. The results thereof are shown in Table 9.

TABLE 9

| Acidic Substance | Amplification Results |
|---|---|
| Addition of Sodium Alginate | ++ |
| No Addition | − |

++: Intensive amplification being observed;
+: Amplification being observed;
±: Slight amplification being observed; and
−: No amplification being observed.

As shown in Table 9, when sodium alginate was added, amplification of a fragment of about 10 kb was confirmed. On the other hand, when there was no addition of sodium alginate, an amplified fragment of about 10 kb could not be confirmed under the above conditions, but when similar PCR was carried out by increasing the amount of template DNA from 10 pg to 1 ng, a desired amplified fragment could be confirmed. Incidentally, even when the amount of template DNA was changed to 1 ng, a desired fragment could not be confirmed in PCR using a standard used amount of TaKaRa EX Taq DNA polymerase. It was shown that rapid PCR could be carried out with a further higher performance by addition of the acidic substance.
(2) Rapid PCR by Combination of Polymerase B with Acidic Substance A PCR reagent mixture comprising λDNA as a template and primers λ1 and λ9 as a primer pair was prepared, and PCR was carried out. The composition for a PCR reagent mixture is as follows.

Composition of PCR Reagent Mixture

Buffer for TaKaRa EX Taq DNA polymerase, 0.2 mM each of dATP, dCTP, dGTP and dTTP, 10 pg of λDNA, 0.5 µl of Polymerase B and 5 pmol each of primers λ1 and λ9 (final volume being 25 µl). Further, 0.75 ng of sulfated-fucose-containing polysaccharide-F or 5 µg of sodium alginate was added, respectively, to the above PCR reagent mixture.

The reaction was carried out in 30 cycles, wherein one cycle of reaction comprises a process consisting of 98° C., 5 seconds–68° C., 3 minutes. After the termination of reaction, 5 µl of the resulting sample was electrophoresed on 1% agarose gel containing ethidium bromide in an amount of 0.00005%, thereby confirming an amplified fragment. The results thereof are shown in Table 10.

TABLE 10

| Acidic Substance | Amount Added | Amplification Results |
|---|---|---|
| Sulfated-Fucose-Containing Polysaccharide-F | 0.75 ng | ++ |
| Sodium Alginate | 5 µg | +++ |
| No Addition | | + |

+ to +++: Extent of amplification is shown in 3 grades.

As shown in Table 10, in case where any of the acidic substances were added, there was confirmed that the amount of a desired amplified fragment of 12 kb was improved, as compared to the case where the acidic substance was not added.

EXAMPLE 7

The effects of the amount of DNA polymerase used for PCR and the acidic substance and its effects on the reaction time were studied.

A PCR reagent mixture comprising λDNA as a template and primers λ1 and λ8 as a primer pair was prepared, and PCR was carried out. In this PCR, TaKaRa EX Taq DNA polymerase and Polymerase B were used. The composition for a PCR reagent mixture is shown below.

Composition of PCR Reagent Mixture

Buffer for TaKaRa EX Taq DNA polymerase, 0.2 mM each of dATP, dCTP, dGTP and dTTP, 10 pg of λDNA, 1.25 U of TaKaRa EX Taq DNA polymerase or 0.5 μl of Polymerase B and 10 pmol each of primers λ1 and λ8 (final volume being 50 μl).

Further, to the above PCR reagent mixture was added 2.5 μg of sodium alginate, to prepare a PCR reagent mixture.

The reaction was carried out in 30 cycles for a total period for PCR of about 80 minutes, wherein one cycle of reaction comprises a process consisting of 98° C., 5 seconds–68° C., 2 minutes. After the termination of reaction, 8 μl of the resulting sample was electrophoresed on 1% agarose gel containing ethidium bromide in an amount of 0.00005%, thereby confirming an amplified fragment. The results thereof are shown in Table 11.

TABLE 11

| Enzyme Used | Amount Added | Amplification Results |
| --- | --- | --- |
| 1.25 U/50 μl (PCR Reagent Mixture) of TaKaRa EX Taq | No Addition | – |
| Polymerase B | No Addition | + |
| Polymerase B | 2.5 μg | ++ |

++: Intensive amplification being observed;
+: Amplification being observed;
+: Slight amplification being observed; and
–: No amplification being observed.

As shown in Table 11, in both cases where Polymerase B was used and where sodium alginate was added to Polymerase B, amplification of an expected fragment of 10 kb was confirmed, and thus rapid PCR could be carried out. Further, the amounts of the amplified products were quantified by using an image analyzer FM-BIO (manufactured by Takara Shuzo Co., Ltd.), and as a result, the amount of the amplified product of the case where sodium alginate was added to Polymerase B was about five times as that compared to the case where no sodium alginate was added, and thus more rapid PCR could be achieved. On the other hand, when 1.25 U of TaKaRa EX Taq DNA polymerase, a standard used amount as described in TaKaRa EX Taq instruction manual, was used alone, amplification by rapid PCR could not be confirmed.

EXAMPLE 8

The effects of the combination of spergualins and acidic substances on the DNA polymerase were studied.

(1) A PCR reagent mixture comprising λDNA as a template and primers λ1 and λ8 as a primer pair was prepared, and rapid PCR was carried out. In this PCR, Polymerase B was used. As the spergualins, 15-deoxyspergualin trihydrochloride was used, and as the acidic substances, sodium alginate (manufactured by Wako Pure Chemicals) was used. The composition for a PCR reagent mixture is shown below.

Composition of PCR Reagent Mixture 50 mM Tris-acetate buffer (pH 8.5), 0.2 mM each of dATP, dCTP, dGTP and dTTP, 3 mM magnesium acetate, 50 mM potassium acetate, 10 pg of λDNA, 10 pmol each of primers λ1 and λ8. To the above PCR reagent mixture was added 0.5 μl of Polymerase B, and further 15-deoxyspergualin trihydrochloride and sodium alginate were added in combination at concentrations shown in Table 10, making up a final volume of 50 μl. In addition, as controls, there were respectively prepared a PCR reagent mixture in which 2.5 μg of sodium alginate was added without adding 15-deoxyspergualin trihydrochloride, and a PCR reagent mixture in which both 15-deoxyspergualin trihydrochloride and sodium alginate were not added.

Rapid PCR was carried out in 30 cycles for a total time period of PCR of about 65.5 minutes, wherein one cycle of reaction comprises a process consisting of 98° C., 5 seconds–68° C., 90 seconds. After the termination of reaction, 8 μl of the resulting sample was electrophoresed on 1% agarose gel containing ethidium bromide in an amount of 0.00005%, thereby confirming an amplified fragment. The results thereof are shown in Table 12.

TABLE 12

| Spergualins/ Acidic Substances (Amount Added) | Amplification Results |
| --- | --- |
| 15-Deoxyspergualin/ Sodium Alginate | |
| 120 μM/2.5 μg | ++++ |
| 100 μM/2.5 μg | ++++ |
| 80 μM/2.5 μg | +++ |
| 60 μM/2.5 μg | ++ |
| 20 μM/2.5 μg | + |
| No Addition/2.5 μg | + |
| No Addition/No Addition | – |

+ to ++++: Extent of amplification is shown in 4 grades.
–: No amplification being observed.

As shown in Table 12, in a system where 15-deoxyspergualin trihydrochloride and sodium alginate were added in combination, the DNA amplification reaction of a 10 kb fragment was enhanced, and thus it was confirmed that rapid PCR for a total time period of PCR of about 65.5 minutes could be achieved. Incidentally, in this example, when the amount of template DNA was increased from 10 pg to 1 ng, a desired amplified product could be confirmed, even in a system where both the spergualin and the acidic substance were not added. On the other hand, even though PCR was carried out under the above conditions using 1.25 U of TaKaRa Taq DNA polymerase and 1 ng of template DNA, a desired amplified product could not be obtained. It was shown that rapid PCR with a further higher performance could be achieved by the addition of the acidic substance.

(2) The effects of the combination of spergualins and acidic substances on the DNA polymerase were studied in a case where template DNA was *E. coli* genomic DNA. The composition for a PCR reagent mixture is shown below.

Composition of PCR Reagent Mixture

The composition for the PCR reagent mixture was the same as that in Item (1) of Example 8, except for using 5 ng of *E. coli* genomic DNA (manufactured by Takara Shuzo Co., Ltd.) and 10 pmol each of primers of Eco-1 and Eco-6. To the above PCR reagent mixture was added 0.5 μl of Polymerase A, and further were added in combination 2.5 μg of sodium alginate and 15-deoxyspergualin trihydrochloride so as to have a final concentration of 1 μM, 5 μM or 10 μM, respectively, making up a final volume of 50 μl. In addition, as controls, there were respectively prepared a PCR reagent mixture in which 2.5 μg of sodium alginate was only added without adding 15-deoxyspergualin trihydrochloride, and a PCR reagent mixture in which both 15-deoxyspergualin trihydrochloride and sodium alginate were not added.

Rapid PCR was carried out in 30 cycles for a total time period of PCR of about 110 minutes, wherein one cycle of reaction comprises a process consisting of 98° C., 5 seconds–68° C., 3 minutes. After the termination of reaction, 8 μl of the resulting sample was electrophoresed on 1% agarose gel containing ethidium bromide in an amount of 0.00005%, thereby confirming an amplified fragment.

The results thereof are shown in Table 13.

TABLE 13

| Spergualins/ Acidic Substances (Amount Added) | Amplification Results |
|---|---|
| 15-Deoxyspergualin/ Sodium Alginate | |
| 10 μM/2.5 μg | ++ |
| 5 μM/2.5 μg | ++ |
| 1 μM/2.5 μg | ++ |
| No Addition/2.5 μg | ± |
| No Addition/No Addition | − |

++: Intensive amplification being observed;
+: Amplification being observed;
±: Slight amplification being observed; and
−: No amplification being observed.

As shown in Table 13, in a system where 15-deoxyspergualin trihydrochloride and sodium alginate were added in combination, the DNA amplification reaction of a 20 kb fragment was enhanced, and thus it was confirmed that rapid PCR for a total time period of PCR of about 110 minutes could be achieved. Incidentally, in this example, when the amount of template DNA was increased from 5 ng to 20 ng, a desired amplified product could be confirmed, even in a system where both the spergualins and the acidic substances were not added. On the other hand, even though PCR was carried out under the above conditions using 1.25 U of TaKaRa Taq DNA polymerase and 1 ng of template DNA, a desired amplified product could not be obtained. It was shown that rapid PCR with a further higher performance could be achieved by the addition of the acidic substance.

EXAMPLE 9

Preparation of Kit (1) Kit in Which Polymerase A or Polymerase B Is Used

A kit (20 reactions) for rapid PCR of the present invention was constructed.

The composition for the kit is shown below:

| 10 × Reaction Buffer | 50 μl |
|---|---|
| 500 mM Tris-Acetate (pH 8.5) | |
| 500 mM Potassium Acetate | |
| 30 mM Magnesium Acetate | |
| 2.5 mM dNTPs Mix | 80 μl |
| (2.5 mM Each of dATP, dCTP, dGTP and dTTP) | |
| DNA Polymerase Enzyme Solution | 10 μl |
| Polymerase A or Polymerase B | |

A PCR reagent mixture was prepared using the above kit. E. coli genomic DNA was used as a template. The composition for the PCR reagent mixture is shown below:

Composition of PCR Reagent Mixture

| 10 × Reaction Buffer | 5 μl |
|---|---|
| dNTPs Mix | 4 μl |
| DNA Polymerase Enzyme Solution | 0.5 μl |
| E. coli genomic DNA | 1 ng |
| Eco-1 Primer | 10 pmol |
| Eco-2 Primer | 10 pmol |
| Sterilized Distilled Water | |
| Final Volume | 50 μl |

The PCR reagent mixture was reacted under the PCR conditions shown in Item (3) of Example 2, and as a result, a desired amplified fragment of about 2 kbp could be confirmed.

(2) Kit in Which Polymerase A or Polymerase B Is Used and Further Comprises Acidic Substance A kit (20 reactions) for rapid PCR of the present invention was constructed.

The composition for the kit is shown below

| 10 × Reaction Buffer | 50 μl |
|---|---|
| 500 mM Tris-Acetate (pH 8.5) | |
| 500 mM Potassium Acetate | |
| 30 mM Magnesium Acetate | |
| 25 μg Sodium Alginate (100 to 150 centipoises) | |
| 2.5 mM dNTPs Mix | 80 μl |
| (2.5 mM Each of dATP, dCTP, dGTP and dTTP) | |
| DNA Polymerase Enzyme Solution | 10 μl |
| Polymerase A or Polymerase B | |

A PCR reagent mixture was prepared using the above kit. λDNA was used as a template. The composition for the PCR reagent mixture is shown below:

Composition of PCR Reagent Mixture

| 10 × Reaction Buffer | 5 μl |
|---|---|
| dNTPs Mix | 4 μl |
| DNA Polymerase Enzyme Solution | 0.5 μl |
| λDNA | 1 ng |
| λ1 Primer | 10 pmol |
| λ8 Primer | 10 pmol |
| Sterilized Distilled Water | |
| Final Volume | 50 μl |

The PCR reagent mixture was reacted under the PCR conditions shown in Example 7, and as a result, a desired amplified fragment of about 10 kbp could be confirmed.

(3) Kit Comprising Polymerase A or Polymerase B, Acidic Substances, and Spergualins A kit (20 reactions) for rapid PCR of the present invention was constructed.

The composition for the kit is shown below

| | |
|---|---|
| 10 × Reaction Buffer | 100 µl |
| 500 mM Tris-Acetate (pH 8.5) | |
| 500 mM Potassium Acetate | |
| 30 mM Magnesium Acetate | |
| 0.04% Sodium Alginate (100 to 150 centipoises) | |
| 1 mM 15 Deoxyspergualin Trihydrochloride | |
| 2.5 mM dNTPs Mix | 160 µl |
| (2.5 mM Each of dATP, dCTP, dGTP and dTTP) | |
| DNA Polymerase Enzyme Solution | 10 µl |
| Polymerase B Concentrate | |

A PCR reagent mixture was prepared using the above kit. λDNA was used as a template. The composition for the PCR reagent mixture is shown below:

Composition of PCR Reagent Mixture

| | |
|---|---|
| 10 × Reaction Buffer | 5 µl |
| dNTPs Mix | 8 µl |
| DNA Polymerase Enzyme Solution | 0.5 µl |
| λDNA | 10 pg |
| λ1 Primer | 10 pmol |
| λ8 Primer | 10 pmol |
| Sterilized Distilled Water | |
| Final Volume | 50 µl |

The PCR reagent mixture was reacted under the PCR conditions shown in Item (1) of Example 8, and as a result, a desired amplified fragment of about 10 kbp could be confirmed.

INDUSTRIAL APPLICABILITY

Rapid PCR which is useful in the field of genetic engineering is provided by the DNA synthesis method and the kit for the DNA synthesis reaction of the present invention, so that there is exhibited an excellent effect that the procedures in the genetic engineering studies and industries which are involved with PCR can be speeded up. In addition, the above-mentioned DNA synthesis method, the kit for the DNA synthesis reaction and the article of manufacture of a PCR agent of the present invention are extremely useful in speeding up and activation of procedures in the entire field in which PCR method can be used. Further, according to the present invention, there can be achieved handling of a large amount of DNA amplified samples in a short period of time and the preparation of a large amount of PCR products. Therefore, the present invention can be utilized in a variety of fields such as the field of genetic diagnosis on the basis of PCR method, DNA chips for diagnosing genes, and the like.

What is claimed is:

1. A DNA synthesis method with a shortened time period for DNA synthesis by polymerase chain reaction (PCR), comprising the steps of:
   carrying out a DNA synthesis by PCR with a reaction mixture comprising: DNA polymerase, template DNA, dNTPs, and primers,
   wherein the amount of DNA polymerase added to said reaction mixture is pre-determined for each specific type of DNA polymerase by carrying out a test PCR reaction under the following conditions (A) and (B):
   (A) reaction mixture: 50 µl volume of a reaction mixture comprising DNA polymerase, 1 ng of genomic DNA from *Escherichia coli,* and 10 pmol each of primers Eco-1 (SEQ ID NO: 10) and Eco-2 (SEQ ID NO: 11); and having a composition suitable for said DNA polymerase; and
   (B) reaction conditions: 35 cycles of PCR, wherein one cycle consists of 99° C., 1 second–66° C., 7 seconds; wherein the amount of DNA polymerase used is that which is sufficient to provide more than 10 ng of amplified DNA fragments of about 2 kb per 50 µl of reaction mixture.

2. The DNA synthesis method according to claim 1, wherein two or more kinds of DNA polymerases are used.

3. The DNA synthesis method according to claim 2, wherein one DNA polymerase comprises 3'→5' exonuclease activity, and the other DNA polymerase comprises substantially no 3'→5' exonuclease activity.

4. The DNA synthesis method according to any one of claims 1 to 3, wherein said PCR is carried out in the presence of an acidic substance and/or a salt thereof.

5. The DNA synthesis method according to claim 4, wherein said acidic substance is an acidic macromolecular substance.

6. The DNA synthesis method according to claim 5, wherein said acidic macromolecular substance comprises a sugar chain backbone.

7. The DNA synthesis method according to claim 5, wherein said acidic substance and/or salt thereof is one or more substances selected from the group consisting of sulfated-fucose-containing polysaccharides, dextran sulfate, carrageenan, heparin, rhamnam sulfate, chondroitin sulfate, dermatan sulfate, (chondroitin sulfate B), heparan sulfate, hyaluronic acid, alginic acid, pectin, polyglutamic acids, polyacrylic acids, polyvinyl sulfates, polystyrene sulfates, DNA and salts thereof.

8. The DNA synthesis method according to claim 1, wherein PCR is carried out in the presence of at least one substance selected from the group consisting of spergualins, degraded products thereof and a salt thereof.

9. A method for determining an effective amount of DNA polymerase useful for performing rapid PCR comprising the steps of:

carrying out a PCR reaction under the following conditions (A) and (B):

(A) reaction mixture: 50 μl volume of a reaction mixture comprising DNA polymerase, 1 ng of genomic DNA from *Escherichia coli,* and 10 pmol each of primers Eco-1 (SEQ ID NO:10) and Eco-2 (SEQ ID NO:11); and having a composition suitable for said DNA polymerase; and (B) reaction conditions: 35 cycles of PCR, wherein one cycle consists of 99° C., 1 second–66° C., 7 seconds; wherein the effective amount of DNA polymerase is determined as that which is sufficient to provide more than 10 ng of amplified DNA fragments of about 2 kb per 50 μl of a reaction mixture.

\* \* \* \* \*

SEQUENCE LISTING

```
<160> NUMBER OF SEQ ID NOS: 14

<210> SEQ ID NO 1
<211> LENGTH: 35
<212> TYPE: DNA
<213> ORGANISM: Artificial Sequence
<220> FEATURE:
<223> OTHER INFORMATION: Artificial sequence derived from lambda DNA.

<400> SEQUENCE: 1
gatgagttcg tgtccgtaca actggcgtaa tcatg                              35

<210> SEQ ID NO 2
<211> LENGTH: 25
<212> TYPE: DNA
<213> ORGANISM: Artificial Sequence
<220> FEATURE:
<223> OTHER INFORMATION: Artificial sequence derived from lambda DNA.

<400> SEQUENCE: 2
ggttatcgaa atcagccaca gcgcc                                         25

<210> SEQ ID NO 3
<211> LENGTH: 23
<212> TYPE: DNA
<213> ORGANISM: Artificial Sequence
<220> FEATURE:
<223> OTHER INFORMATION: Artificial sequence derived from lambda DNA.

<400> SEQUENCE: 3
gcgtaccttt gtctcacggg caa                                           23
```

```
<210> SEQ ID NO 4
<211> LENGTH: 22
<212> TYPE: DNA
<213> ORGANISM: Artificial Sequence
<220> FEATURE:
<223> OTHER INFORMATION: Artificial sequence derived from lambda DNA.

<400> SEQUENCE: 4
gatagctgtc gtcataggac tc                                              22

<210> SEQ ID NO 5
<211> LENGTH: 23
<212> TYPE: DNA
<213> ORGANISM: Artificial Sequence
<220> FEATURE:
<223> OTHER INFORMATION: Artificial sequence derived from lambda DNA.

<400> SEQUENCE: 5
cttaaccagt gcgctgagtg act                                             23

<210> SEQ ID NO 6
<211> LENGTH: 28
<212> TYPE: DNA
<213> ORGANISM: Artificial Sequence
<220> FEATURE:
<223> OTHER INFORMATION: Artificial sequence derived from lambda DNA.

<400> SEQUENCE: 6
ttgccacttc cgtcaaccag gcttatca                                        28

<210> SEQ ID NO 7
<211> LENGTH: 29
<212> TYPE: DNA
<213> ORGANISM: Artificial Sequence
<220> FEATURE:
<223> OTHER INFORMATION: Artificial sequence derived from lambda DNA.

<400> SEQUENCE: 7
tgtccgtcag ctcataacgg tacttcacg                                       29

<210> SEQ ID NO 8
<211> LENGTH: 28
<212> TYPE: DNA
<213> ORGANISM: Artificial Sequence
<220> FEATURE:
<223> OTHER INFORMATION: Artificial sequence derived from lambda DNA.

<400> SEQUENCE: 8
atatctggcg gtgcaatatc ggtactgt                                        28

<210> SEQ ID NO 9
<211> LENGTH: 28
<212> TYPE: DNA
<213> ORGANISM: Artificial Sequence
<220> FEATURE:
<223> OTHER INFORMATION: Artificial sequence derived from lambda DNA.

<400> SEQUENCE: 9
gacaatctgg aatacgccac ctgacttg                                        28

<210> SEQ ID NO 10
<211> LENGTH: 35
<212> TYPE: DNA
<213> ORGANISM: Artificial Sequence
<220> FEATURE:
<223> OTHER INFORMATION: Artificial sequence derived from E. coli.
```

```
-continued

<400> SEQUENCE: 10
ggtggcgatg caaatgcaat cttcgttgcc ccaac                              35

<210> SEQ ID NO 11
<211> LENGTH: 35
<212> TYPE: DNA
<213> ORGANISM: Artificial Sequence
<220> FEATURE:
<223> OTHER INFORMATION: Artificial sequence derived from E. coli.

<400> SEQUENCE: 11
ttatgtatgc cgcgtatcag cttcatgtct ggctc                              35

<210> SEQ ID NO 12
<211> LENGTH: 35
<212> TYPE: DNA
<213> ORGANISM: Artificial Sequence
<220> FEATURE:
<223> OTHER INFORMATION: Artificial sequence derived from E. coli.

<400> SEQUENCE: 12
gagccagaca tgaagctgat acgcggcata cataa                              35

<210> SEQ ID NO 13
<211> LENGTH: 35
<212> TYPE: DNA
<213> ORGANISM: Artificial Sequence
<220> FEATURE:
<223> OTHER INFORMATION: Artificial sequence derived from E. coli.

<400> SEQUENCE: 13
atcatctaac ctgttctgga aaacgcttgc gcagc                              35

<210> SEQ ID NO 14
<211> LENGTH: 35
<212> TYPE: DNA
<213> ORGANISM: Artificial Sequence
<220> FEATURE:
<223> OTHER INFORMATION: Artificial sequence derived from E. coli.

<400> SEQUENCE: 14
tgcaaatact tctgcgccaa tgcggcattt gaagt                              35
```